(12) United States Patent
Schneider

(10) Patent No.: US 10,468,129 B2
(45) Date of Patent: Nov. 5, 2019

(54) BIOMETRIC MEDICAL ANTIFRAUD AND CONSENT SYSTEM

(71) Applicant: David Lyle Schneider, Sai Kung (HK)

(72) Inventor: David Lyle Schneider, Sai Kung (HK)

(*) Notice: Subject to any disclaimer, the term of this patent is extended or adjusted under 35 U.S.C. 154(b) by 53 days.

(21) Appl. No.: 15/707,431

(22) Filed: Sep. 18, 2017

(65) Prior Publication Data

US 2018/0082026 A1    Mar. 22, 2018

Related U.S. Application Data

(60) Provisional application No. 62/395,514, filed on Sep. 16, 2016.

(51) Int. Cl.
| | |
|---|---|
| *H04L 29/00* | (2006.01) |
| *G16H 10/60* | (2018.01) |
| *H04L 9/32* | (2006.01) |
| *H04L 9/06* | (2006.01) |
| *H04L 9/08* | (2006.01) |
| *G06F 21/32* | (2013.01) |
| *G06F 21/62* | (2013.01) |
| *G06F 21/64* | (2013.01) |

(52) U.S. Cl.
CPC ............ *G16H 10/60* (2018.01); *G06F 21/32* (2013.01); *G06F 21/6245* (2013.01); *G06F 21/64* (2013.01); *H04L 9/06* (2013.01); *H04L 9/0866* (2013.01); *H04L 9/0894* (2013.01); *H04L 9/3231* (2013.01); *H04L 2209/88* (2013.01)

(58) Field of Classification Search
CPC ...... G16H 10/60; G06F 21/32; G06F 21/6245; G06F 21/64; H04L 9/06; H04L 9/0866; H04L 9/0894; H04L 9/3231; H04L 2209/88
See application file for complete search history.

(56) References Cited

U.S. PATENT DOCUMENTS

| | | | | |
|---|---|---|---|---|
| 6,882,859 | B1* | 4/2005 | Rao | G06F 3/023 455/550.1 |
| 7,305,562 | B1* | 12/2007 | Bianco | H04L 63/08 709/229 |
| 9,294,452 | B1* | 3/2016 | Jakobsson | H04L 63/08 |
| 2004/0026496 | A1* | 2/2004 | Zuili | G06Q 20/341 235/379 |
| 2004/0099731 | A1* | 5/2004 | Olenick | G07F 17/26 235/380 |
| 2004/0104266 | A1* | 6/2004 | Bolle | G06F 21/6245 235/382 |
| 2004/0246095 | A1* | 12/2004 | Berger | G07C 9/00158 340/5.22 |
| 2006/0242423 | A1* | 10/2006 | Kussmaul | G06F 21/32 713/182 |
| 2010/0312548 | A1* | 12/2010 | Herley | G06F 16/9032 704/9 |

(Continued)

*Primary Examiner* — Ghodrat Jamshidi
(74) *Attorney, Agent, or Firm* — Wayne & Ken, LLC; Tony Hom

(57) ABSTRACT

A specialized apparatus for recording medical transactions designed to protect patient privacy when necessary to record private biometric individual data. The mechanisms and proprietary methods scramble the biometric data within the recording device, unrecoverable when leaving recording device with high assurance, yet an audit copy can forward to outside permanent storage and systems.

1 Claim, 3 Drawing Sheets

(56) References Cited

U.S. PATENT DOCUMENTS

| | | | |
|---|---|---|---|
| 2013/0050652 A1* | 2/2013 | Wharton | H04N 5/2251 352/34 |
| 2013/0231954 A1* | 9/2013 | Bryant | G06F 21/32 705/3 |
| 2014/0046842 A1* | 2/2014 | Irudayam | G07F 19/202 705/43 |
| 2015/0223057 A1* | 8/2015 | Dellarciprete | H04W 12/02 455/410 |
| 2015/0235226 A1* | 8/2015 | Mao | G06Q 20/40145 705/72 |
| 2015/0321606 A1* | 11/2015 | Vartanian | G02B 27/0101 348/148 |
| 2016/0364723 A1* | 12/2016 | Reese | G06Q 20/38215 |
| 2016/0364729 A1* | 12/2016 | Ruparelia | G06Q 20/40145 |
| 2017/0177855 A1* | 6/2017 | Costa Faidella | G06F 21/45 |
| 2017/0324750 A1* | 11/2017 | Khan | H04L 63/123 |

\* cited by examiner

BIOMETRIC MEDICAL ANTIFRAUD AND CONSENT SYSTEM

CROSS-REFERENCE TO RELATED APPLICATIONS

This application claims benefit of 2016 provisional filing No. 62/395,514.

BACKGROUND OF THE INVENTION

Medical device technology and the systems providing healthcare service to public populations have progressed exponentially during recent years following computing revolution in the early 1970's and personal computing revolutions since the 1980's.

This is well-known history and the public health benefits deriving from these technical and informational advancements are very important and significant for citizens of many countries. However, along with this progress, there are unanticipated challenges created by the complexity and interconnectedness of medical and healthcare industry systems.

One recent risk has been the proliferation of 'hacker' activity with purpose of causing damage and disruption to others based upon personal, political, nation-state and economic objectives. For medical industry, this means patients have valid concerns about the privacy, accuracy and disclosure of their very sensitive health-related and person-related 'information.'

Current industry trends address these problems with ubiquitous security solutions focused on applications, databases, firewalls, and activity alarm systems. One part of the solution is, for example, proprietary encrypting hard drives which are manufactured and installed in servers and workstations to protect against unauthorized disclosure. In 2017, there was a recent data breach at a major financial data collector resulting in over 140 million detailed financial records—data that will be used in theft and impersonation for fraudulent gain. So in short, this is a public problem that requires multiple solutions to protect privacy of individuals and patients. Privacy expectations are extremely sensitive in medical healthcare.

BRIEF SUMMARY OF INVENTION

Purpose is to improve patient privacy when using a biometric signature such as fingerprints, face scans and related characteristics when recorded into a computing system. A segregated and custom-purpose hardware device can scramble and encode private information in a manner that cannot be deciphered outside of the device. This therefore allows for permanent storage of such biometric information (scrambled without external cipher keys) without risk of viruses, theft and loss of system data from cloud, private network, or insurance industry data warehouse systems. Present invention claims custom-purpose apparatus and methods, and does not discuss the complex systematic and biometric workflow systems beyond the invention boundaries. There are numerous possibilities, variations and vendors in the medical and finance marketplace with biometric reader equipment.

DETAILED DESCRIPTION OF INVENTION

Figure 1:
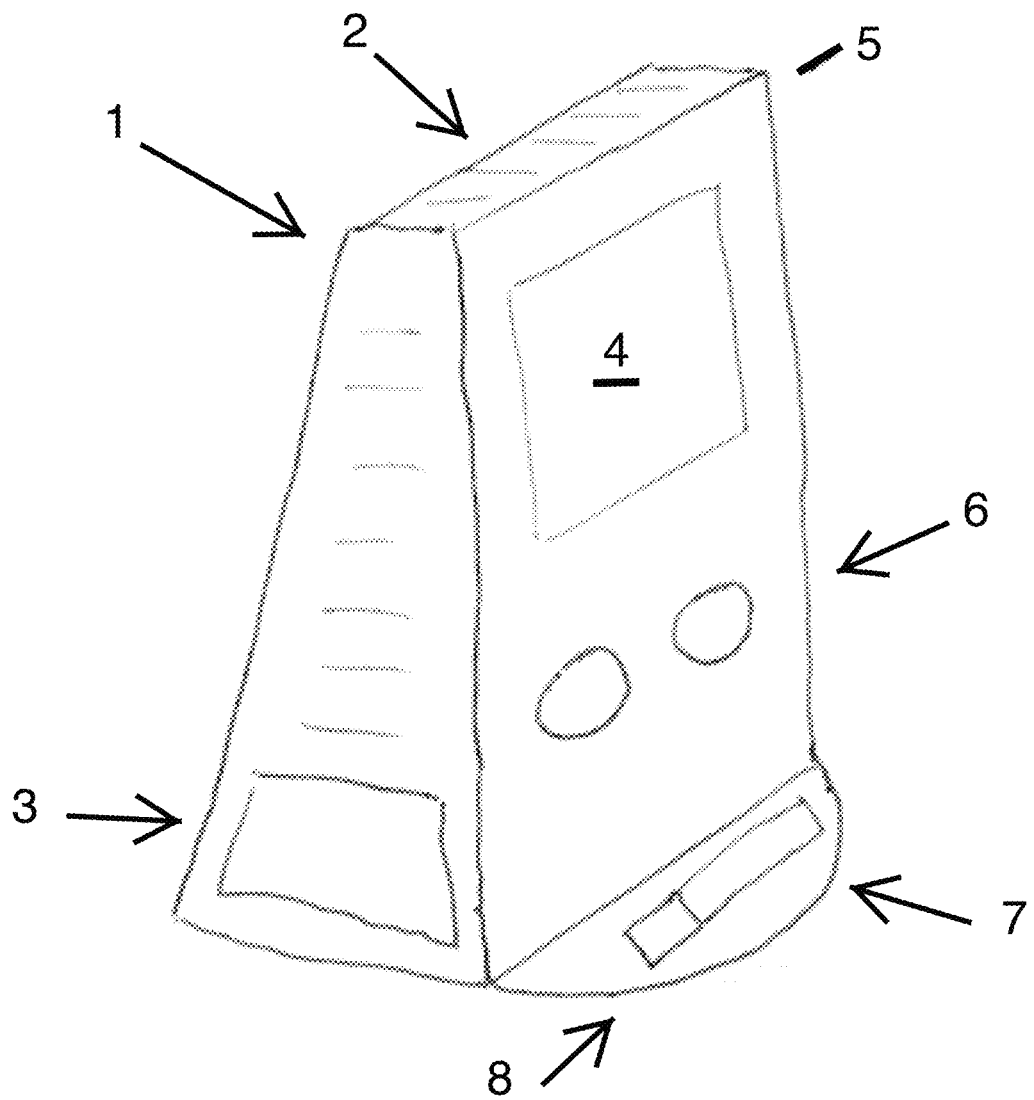
FIG. 1—Physical characteristics of preferred embodiment.
Figure 2:
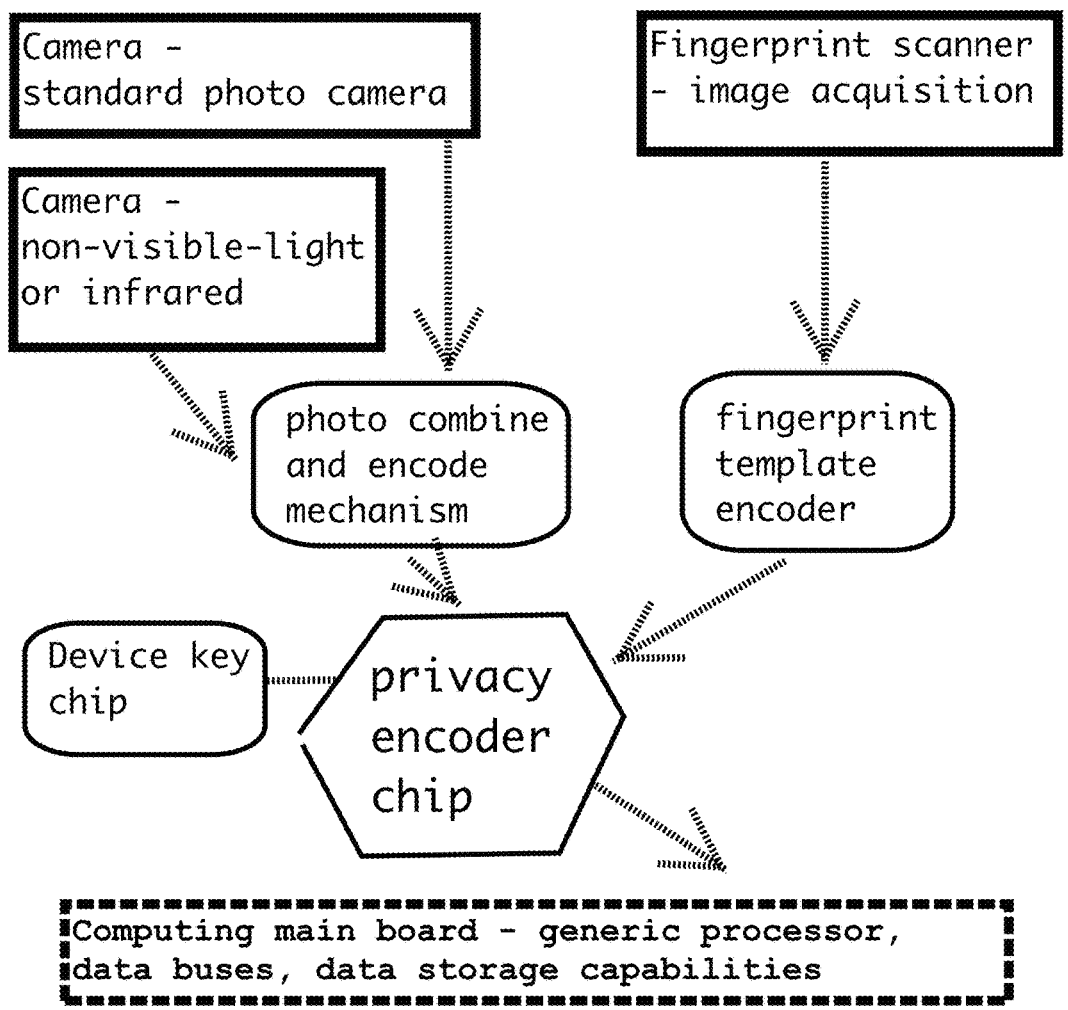
FIG. 2—Hardware mechanisms in recording apparatus.
Figure 3:
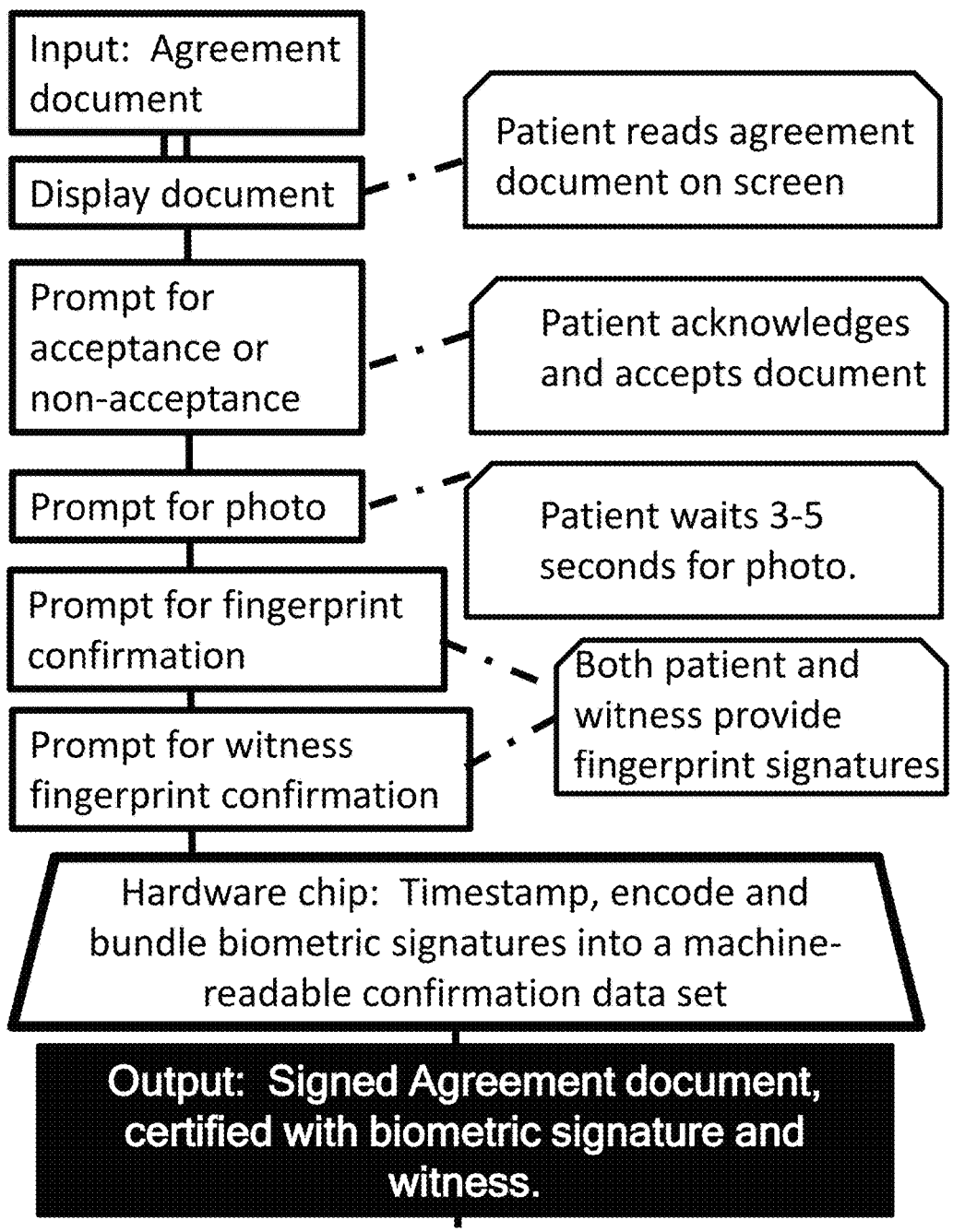
FIG. 3—Alternate embodiment functionality that records a real-time transaction for audit purpose.

Present invention is one highly-specific, specialized apparatus designed to protect patient privacy while recording some highly private and personal data about an individual. This is a challenging solution considering the high-level government and insurance industry goals, in a systematic way, demand collecting biometric information (i.e. fingerprints, photographs, other data based upon personal characteristics of an individual).

Present invention acknowledges necessity of positive identification readers which can improve safety and help audit the financial fraud abuses in a complex, multi-billion dollar industry.

Preceding technologies cited in the marketplace are fingerprint reader devices, biometric lock devices, access-authorization-auditing electronic system access controls, and numerous healthcare data processing systems and databases. Listing below includes general state of the prior art related to this subject: IBM thinkpad laptop integrated fingerprint readers.

Fingerprint reader hardware in law enforcement and customs identification, various.

Biometric door locks, various.

Systematic face scan, various.

Financial industry transaction systems, various.

NSA Type I, Type II hardware encryption, various.

DETAILED DESCRIPTION OF DRAWINGS

FIG. 1

(1) Sealed enclosure with filtered vents (2) Exhaust vent screen (3) Intake vent filter, necessary to remove particulate matter and improve reliability of device in imperfect and hot field conditions.

(4) Instructions display screen, 4×4 or various, displays written instructions provided to the patient.

(5) Metal heat-sink casing for camera heat.

(6) Camera module, normal visible light; and second Camera module, thermal, infrared or non-visible-light spectrum.

(7) Fingerprint bar reader, with multiple-finger scanning.

(8) Thumbprint reader, single-finger scanning.

FIG. 2

This diagram indicates the relationship and order of hardware mechanisms in the recorder device. The data flow begins at the top with an acquisition hardware, where raw biometric data is input. This unprotected data is encoded by hardware before delivery to temporary storage on an encryption chip mechanism. Device utilizes a private encryption key which is known only to the device. The hardware encryption mechanism is marked Privacy Chip to illustrate this final step.

FIG. 3

Alternate embodiment: This example chart demonstrates how a private biometric signature can be used to confirm a real-time medical transaction. For medical fraud prevention, these steps demonstrate how a patient can review a document and then certify with a witness, using a real-time apparatus, with hardware encryption.

I claim:

1. A computer-implemented recording method within a dedicated device for recording a medical transaction declaration record in real-time where a patient's private information is encoded and encrypted to prevent forgery tampering, the dedicated device including at least two biometric readers, a camera, a display screen, and an encryption module for encoding and encrypting record data in accordance with a private encryption key unique to the recording of the medical transaction declaration record, the method comprising:

receiving an input of an agreement document and providing a visual display of the agreement document on the display screen;

prompting for an affirmative or negative response from the patient through the display screen;

activating the camera to capture a photograph of the patient;

activating the biometric readers to record biometric fingerprint signatures of the patient and a witness;

time-stamping and encoding the biometric fingerprint signatures into a machine-readable confirmation data set, and electronically determining that the biometric fingerprint signatures are recorded within 1000 ms (1 second);

merging the biometric fingerprint signatures from the patient and the witness to generate a signed agreement document; and outputting the signed agreement document to computing main board, certified with the biometric fingerprint signatures of the patient and the witness.

* * * * *